United States Patent [19]
Hessel

[11] Patent Number: 5,623,946
[45] Date of Patent: *Apr. 29, 1997

[54] TUBULAR PROTECTIVE DEVICE FOR PROTECTION AGAINST TRANSFER OF INFECTIOUS MATTER DURING SEXUAL INTERCOURSE

[75] Inventor: Jasse Hessel, Oakley Hill, Denmark

[73] Assignee: Chartex International Plc., United Kingdom

[*] Notice: The term of this patent shall not extend beyond the expiration date of Pat. No. 5,094,250.

[21] Appl. No.: 250,660

[22] Filed: May 27, 1994

Related U.S. Application Data

[63] Continuation of Ser. No. 840,921, Feb. 25, 1992, abandoned, which is a continuation of Ser. No. 27,842, Mar. 8, 1993, abandoned, which is a continuation-in-part of Ser. No. 621,850, Dec. 4, 1990, Pat. No. 5,094,250, which is a continuation of Ser. No. 148,992, Jan. 27, 1988, Pat. No. 4,976,273, which is a continuation of Ser. No. 58,766, Jun. 5, 1987, Pat. No. 4,735,621.

[51] Int. Cl.$^6$ ........................................ A61F 6/04
[52] U.S. Cl. .................................. 128/844; 128/918
[58] Field of Search ........................ 128/842, 844, 128/918; 604/347–353

[56] References Cited

U.S. PATENT DOCUMENTS

| | | |
|---|---|---|
| 1,687,717 | 10/1928 | Epstein . |
| 2,577,345 | 12/1951 | McEwen ................................ 128/844 |
| 2,586,674 | 2/1952 | Lönne ................................ 128/844 |
| 3,130,721 | 4/1964 | Young ................................ 128/844 |
| 3,351,060 | 11/1967 | Woskin . |
| 3,499,447 | 3/1970 | Mattes et al. . |
| 3,512,528 | 5/1970 | Whitehead et al. . |
| 3,534,737 | 10/1970 | Jones, Sr. . |
| 3,536,066 | 10/1970 | Ludwig ................................ 128/844 |
| 3,709,220 | 1/1973 | Boyden . |
| 3,983,875 | 10/1976 | Truman . |
| 4,048,998 | 9/1977 | Nigro . |
| 4,540,409 | 9/1985 | Nystrom et al. . |
| 4,576,156 | 3/1986 | Dyck ................................ 128/844 |
| 4,610,659 | 9/1986 | Friese . |
| 4,620,534 | 11/1986 | Zartman . |
| 4,756,156 | 7/1988 | Dyck ................................ 128/844 |
| 4,781,709 | 11/1988 | Grubman ................................ 128/844 |
| 4,794,920 | 1/1989 | Robichaud ................................ 604/349 |
| 4,798,600 | 1/1989 | Meadows . |
| 4,815,151 | 3/1989 | Ball ................................ 604/349 |
| 4,834,114 | 5/1989 | Boarman ................................ 128/844 |
| 4,840,624 | 6/1989 | Lee ................................ 604/353 |
| 4,846,802 | 7/1989 | Sanders, III . |
| 4,867,176 | 9/1989 | Lash . |

FOREIGN PATENT DOCUMENTS

| | | |
|---|---|---|
| 1389477 | 1/1965 | France . |
| 589643 | 4/1933 | Germany . |
| 0593216 | 2/1934 | Germany ................................ 128/834 |
| 3723458 | 1/1989 | Germany . |
| 24-2703 | 9/1924 | Japan . |
| 9-6311 | 5/1934 | Japan . |
| 22-529 | 4/1947 | Japan . |
| 27-4688 | 6/1952 | Japan . |
| 47-11199 | 2/1971 | Japan . |
| 47-9299 | 2/1971 | Japan . |

*Primary Examiner*—Michael A. Brown
*Attorney, Agent, or Firm*—Banner & Allegretti, Ltd.

[57] ABSTRACT

A thin-walled, condom-like tubular protective device for protection against the transfer of infectious matter during sexual intercourse is disclosed. The condom-like device has an open end a collar-shaped outwardly extending portion with an apparatus for radially stretching the collar and has an inner diameter which is sufficiently large to permit movement of a penis with respect to the protective device during coitus.

2 Claims, 2 Drawing Sheets

TUBULAR PROTECTIVE DEVICE FOR PROTECTION AGAINST TRANSFER OF INFECTIOUS MATTER DURING SEXUAL INTERCOURSE

This application is a continuation of U.S. patent application Ser. No. 840,921, filed Feb. 25, 1992, now abandoned, which is a continuation of U.S. patent application Ser. No. 027,842, filed Mar. 8, 1993, now abandoned, which is a continuation-in-part of U.S. patent application Ser. No. 621,850, filed Dec. 4, 1990, now U.S. Pat. No. 5,094,250, which is a continuation of U.S. Ser. No. 148,992, filed Jan. 27, 1988, which is U.S. Pat. No. 4,976,273, which is a continuation of U.S. patent application Ser. No. 058,766, filed Jun. 5, 1987, now U.S. Pat. No. 4,735,621, herein incorporated by reference.

BACKGROUND OF THE INVENTION

1. Field of the Invention

The present invention relates to a tubular protective device or condom-like device for protection against the transfer of infectious matter during sexual intercourse. Specifically, the invention relates to a thin-walled tubular protective device having a closed end and an open end wherein the open end has an outwardly extending portion with means for keeping the open end radially stretched.

2. Description of the Background Art

Condoms, besides being contraceptives, offer protection during sexual intercourse against the transfer of infectious matter such as bacterial and vital microbes that cause venereal diseases. After the appearance of AIDS great efforts have been made by various health authorities to impel people to increase the use of condoms during sexual intercourse in order to prevent the spread of this fatal disease.

Condoms comprise a thin tubular casing, that is typically manufactured from latex and that has an open end and a closed end. Condoms are drawn over the penis before coitus. The casing has an inner diameter that is adapted to allow the condom to fit tightly on the penis. At the open end of a condom an elastic, flexible ring or rolled portion of latex is usually provided. This ring portion is the same diameter as the tubular casing of the condom. This elastic ring portion serves primarily to secure the condom on the penis and to prevent leakage of semen from the interior of the condom. Such elastic ring portions contract the open end of a condom onto the penis and do not radially extend the open end of the condom.

It is a generally accepted that the AIDS virus can only be transferred through contact with the carrier's blood or blood plasma. During sexual intercourse such a transfer of the AIDS virus occurs when lesions of the carrier contact the mucous membrane or skin of the carrier's partner. Such a transfer of the AIDS virus is especially likely to occur around the root or base of the penis and the vulva. There is a risk that lesions in these areas can be caused to bleed during sexual intercourse. When using a standard condom, these areas are unprotected or unshielded by the condom and consequently a condom does not offer full protection against the transfer of infectious matter such as the AIDS virus.

Numerous attempts have been made to design a condom or condom-like device that provides effective contraception and/or more protection against the transfer of infectious matter than the standard condom. A sampling of these attempts is described below.

U.S. Pat. No. 4,004,591 to Freimark discloses a birth control device. This birth control device is a female condom made of a strong rubber, plastic, or other similar material. This condom has a rigid, ring-like rim that is bent or scalloped. This rim can be a wire. The rim is not adapted to radially extend the open end of this device because this device is a hard molded material and not flexible. The cross-sectional dimensions of this condom are disclosed as being sufficiently large to easily accommodate the average male width with some additional clearance space. The primary function of this device is to prevent unwanted pregnancy. This device is useful in preventing the spread of venereal disease. This device provides no means to prevent an exchange between partners of secreted fluids that may contain venereal disease. Additionally, this birth control device is intended for use by females, but includes no means to secure or maintain the device in the vagina.

U.S. Pat. No. 4,630,602 to Strickman et al. discloses a disposable contraceptive cervical barrier. The cervical barrier of this invention is similar to standard diaphrams in size and design. This cervical barrier contains various "cavities for cells" that can hold spermicidal lubricants. These spermicidal lubricants can also be placed in numerous grooves within the body of the cervical barrier. Urethane polymers are used to make the device. The cervical barrier of this invention, unlike a condom, has no tubular side walls to prevent the exchange between partners of secretions that can contain a venereal disease.

U.S. Pat. No. 3,536,066 to Ludwig discloses a human birth control appliance. The appliance of this patent protects both partners from any dermic contact. This device is large and awkward to use.

U.S. Design Pat. No. 254,808 to Meldahl discloses a design for a male contraceptive. This contraceptive appears to be larger in diameter than the average condom, but this contraceptive has no means at its open end to aid in the prevention of the spread of venereal disease.

The industry is lacking a simple, easy-to-use device that provides protection against the transfer of body fluids between partners during sexual intercourse, especially between the base of the penis and the vulva.

SUMMARY OF THE INVENTION

The invention is a tubular protective device for protection against a transfer of infectious matter during sexual intercourse. The protective device comprises a flexible, thin-walled, tube that is closed at one end and has at an open end a collar-shaped, outwardly extending portion with means for radially stretching the collar or open end. The inner diameter of the device is sufficiently large to permit movement of a penis with respect to the tubing of the device during coitus or sexual intercourse.

A desirable embodiment of the invention is a tubular protective device that comprises a flexible, thin-walled tube having a closed end, an open end, and a first diameter. This embodiment of the invention further has an outwardly extending collar-shaped means of a second diameter for radially stretching the open end wherein the first diameter of the tube is smaller than the second diameter of the means for radially stretching and the first diameter is sufficiently large to permit movement of a penis within the tube of the device during sexual intercourse.

A desirable embodiment of the invention, that is adapted to function as a female condom like device, is a tubular protective device that comprises a flexible, thin-walled tube having a closed end and an open end. This embodiment also has a first outwardly extending ring-shaped means that is adapted for radially extending the open end and a second outwardly extending ring-shaped means that is adapted for radially extending the closed end. The second ring-shaped means secures or maintains the device in the vagina in a manner similar to a diaphram.

BRIEF DESCRIPTION OF THE DRAWINGS

FIG. 2b is a three dimensional side view of the protective device of FIG. 2a.

DESCRIPTION OF THE PREFERRED EMBODIMENTS

Figure 1:
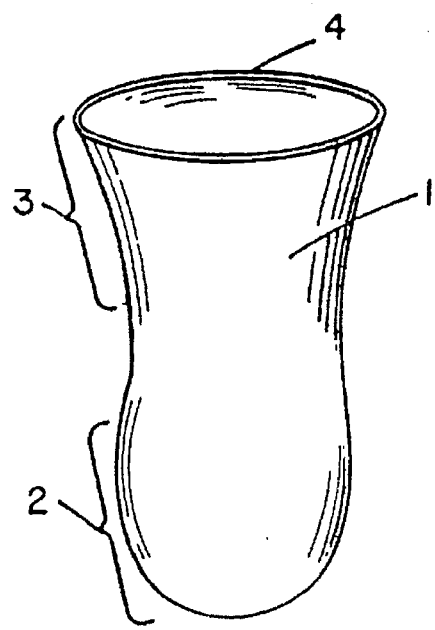
FIG. 1 is a three dimensional view of the protective device of this invention.

The invention is a tubular protective device for protection against a transfer of infectious matter during sexual intercourse. The device comprises a flexible, thin-walled tube closed at one end and open at a second end. The open end has a collar-shaped, outwardly extending portion and a means for radially stretching the collar-shaped portion or open end. The device has an inner diameter of sufficiently large dimension to permit movement of a penis with respect to the protective device during sexual intercourse. Besides protecting against a transfer of infectious matter, the protective device is a contraceptive and, due to the presence of the collar-shaped portion of the device, the contraceptive effect is even more efficient than that obtained with standard condoms because of the additional protection provided around the vulva.

The invention is based on the discovery that a particularly good protection against the transfer of infectious matter, and especially the AIDS virus, is obtained if a condom-like or tubular protective device is used during sexual intercourse that has at its open end an outwardly extending collar that is connected to a rigid ring-like means. The ring-like means is adapted to maintain the collar of the device in a radially extended or stretched condition. The collar is preferably of a dimension that covers the vulva completely. The tubular protective device desirably has a sufficiently large inner diameter to allow movement of a penis with respect to the walls of the tubular device. The walls of the tubular device are held in a relatively immovable state or condition against the vaginal wall. The collar covering the vulva is, also, essentially immovable with respect to the vulva during coitus.

The flexible, thin-walled tube of the invention is desirably cylindrical in shape and has an open end and a closed end. The tube is preferably made from a natural or synthetic polymer material. Desirable polymer materials are members selected from the group consisting of latex, polyethylenes, polyurethanes, and derivatives based upon these polymers. The preferred material is a polyether polyurethane that has a soft, nonadhesive "hand feel". Other polymers or plastics such as polyolefins can be used to manufacture the tube of this device.

The tube of this device can be manufactured by numerous methods that are standard within the industry that fabricates items from polymer materials. The particular method chosen to manufacture the device of this invention varies with the particular polymer material chosen. An acceptable method of manufacturing the device can include curing a polymer material, such as latex, on a mold that has been dipped into a container of heated, liquified polymer material. Other methods can include either vacuum forming or blow molding a sheet of heated polymer material into or onto a mold. Vacuum forming and blow molding are desirable with synthetic polymer materials such as polyurethanes.

The preferred method for manufacturing the device, when it is made of a synthetic polymer such as polyurethane, is to heat seal two layered sheets of the polymer material together to form the desired shape of the device. Heat sealing methods can be undesirable if caution is not exercised during the process. This is because these methods can leave hardened seams that can potentially irritate skin and mucous membrane surfaces. Additionally, the seams are subject to leakage and tearing if the heat sealing method is performed at an undesirably high temperature. Heat sealing methods, however, are desirable because the sheets of polymer material is not stretched during the manufacturing of the device and a consistent wall thickness for the device can be obtained.

The wall thickness of the condom-like device can vary greatly. Typically, thinner wall thicknesses for the device allow more sensitivity during coitus. Wall thicknesses can be varied depending upon the strength of the polymer material that is chosen for the device. Preferably, a wall thickness for the device is between 20 and 60 microns ($\mu$m) for synthetic materials such as polyurethanes and 30 to 90 microns for natural materials such as latex. A wall thickness, regardless of the material from which the device is manufactured, must provide a tensile strength of at least 17 MPa when tested less than 12 months after manufacture and at least 15 MPa when tested 12 months or more after manufacture in order to comply with the standards of the American Society for Testing and Materials.

The internal or inner diameter of the tubular protective device in its unstretched state is desirably of a sufficiently large dimension to permit movement of a penis with respect to the protective device during sexual intercourse. The invention can have an inner diameter that causes the condom to be form fitting, but form fitting condom devices do not permit adequate sensitivity for the male during sexual intercourse. This is because a form fitting condom moves with the penis and prevents direct contact between the vaginal wall and the glans area during intercourse. This undesirable effect of form fitting condoms discourages their use by many members of the public. A condom-like device having a large inner diameter merely functions as a liner for the vaginal wall. In this situation the device is relatively stationary to the vaginal wall and the glans is in direct contact with the surface against which it is moving. This structural arrangement, wherein the inner diameter of the condom-like device is larger than a penis, provides greater sensitivity for both partners.

Desirably any diameter of the tube below the outwardly extending collar-shaped means for radially stretching the open end, such as an elastic ring, is smaller than a second diameter of the means for radially stretching the open end and the first diameter is sufficiently large to permit movement of a penis-within the tube during sexual intercourse.

Standards within the industry for condoms, typically, do not define the inner diameter of a condom, but define the acceptable width of the condom when it is laid flat on a surface. A condom having a width of about 47 millimeters to about 51 millimeters is considered, within the industry, to be form fitting. Contoured or loose fitting condoms have a width of about 50 millimeters to about 54 millimeters. For this invention an acceptable width is at least about 50 millimeters in an unstretched state along the entire length of the tube. A desirable range for the width of the condom-like device of this invention is between about 55 millimeters and about 85 millimeters.

The collar-shaped, outwardly extending portion of the protective device has a means for radially stretching or extending the collar, such as a ring. Furthermore, the ring serves to prevent the open end of the tubular protective device from being pushed into the vagina during sexual intercourse.

The means for extending the collar is desirably a semi-rigid ring or ring-like member. In the most desirable embodiments of the invention, the ring is manufactured from a suitable plastic as a separate part. The invention can be made wherein the means for extending the collar is integrally formed from the same material from which the walls of the device are formed. Such a structure can be formed by rolling the polymer material that forms the walls of the device from the open end of the tube so as to form a ring of material. This ring of material can be maintained by heating the ring or using an adhesive to maintain the ring and prevent it from unrolling.

The diameter of the means for radially stretching the collar is desirably large enough to prevent the exchange of secretions between partners during sexual intercourse. The diameter of the means for radially stretching the collar is desirably large enough such that the vulva and the base of the penis are covered by the extended collar. The preferred embodiments of the invention have a first diameter for the tube of the device and a second diameter for the means for radially stretching the collar such as an elastic ring wherein the second diameter is larger than the first diameter. Acceptable diameters for the means for radially stretching the collar of the device are at least about 50 millimeters and desirably between about 60 and about 75 millimeters. Preferably, the collar is conically shaped and when a tubular protective device having an inner diameter of approximately 50 millimeters is used, the collar, supported by the means for radially stretching, preferably has an inner diameter of approximately 75 millimeters.

Insertion into the vagina of the tubular device of the invention can be done by either the man or the woman. The device can be inserted in the traditional manner by the male partner placing the device over the penis before coitus. The female partner can insert the device with a finger or by means of a insertion probe or applicator.

In order to prevent the tubular protective device from unintentionally slipping out of the vagina once inserted by the female partner has occurred, a means for retaining the device in the vagina such as a circular elastic member or an elastic ring can be used. This member or ring can be connected to the internal or external wall at or near the closed end of the device. After being placed correctly in the vicinity of the uterus, the circular elastic member or an elastic ring is maintained within the vagina in the same manner as a diaphragm.

In order to facilitate insertion of the tubular protective device into the vagina, the closed end of the device can be enclosed by a sheathing which is axially movable relative to the protective device. During the insertion of the protective device into the vagina, the sheathing is moved backwards and, thus it opens for insertion of the closed end of the protective device. Such a sheathing is not typically present if a means for retaining the device in the vagina such as an elastic ring is present.

Prior to or in connection with the insertion of the tubular protective device, a lubricant is preferably applied to at least the inner side of the device to reduce friction during contact with the penis. If desired, a lubricant can also be applied to the exterior side of the device. Application of a lubricant to the inner side of the tubular protective device can facilitate the insertion of the device into the vagina. Selection of a desirable lubricant can vary greatly. The selection of a lubricant depends in part upon the compatibility of the lubricant with the polymer material used to manufacture the device. Desirable lubricants can include ointments, creams, or water-based mucilages or mucilage-like substances such as cellulose-based lubricants.

The invention is described in more detail with reference to the figures which show desirable embodiments of both the male and female tubular protective devices according to the invention.

FIG. 1 discloses a thin-walled tubular device 1 having a closed end 2 that is rounded. At the end of the thin-walled tubular device 1 that is opposite to the closed end 2, the thin-walled tubular device i continues into a conically-shaped collar 3 ending in an elastic ring 4. The composition and dimensions of the elastic ring 4 are adapted such that the collar 3 is stretched and maintained in a stretched condition. The flexible material used to form the thin-walled tubular device 1 of this embodiment overlaps or encapsulates the elastic ring 4. The thin-walled tubular device of this figure functions as a male condom-like device.

Figure 2A:
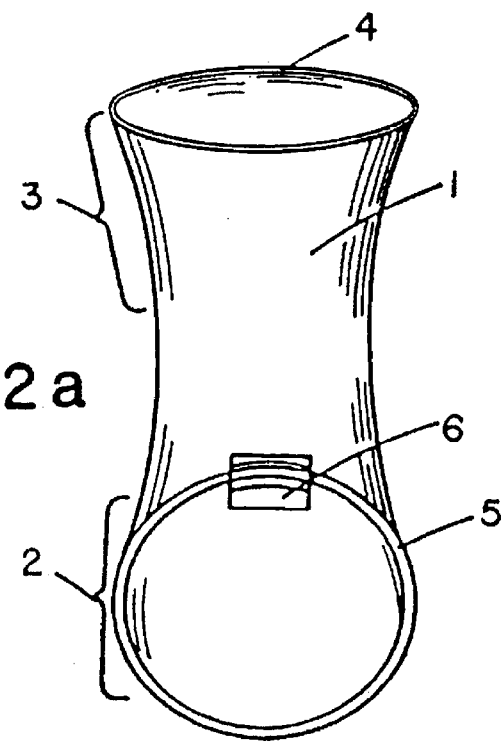
FIG. 2a is a three dimensional front view of the invention that is adapted to function as a female condom-like or protective device.

FIG. 2a discloses a front view of a thin-walled tubular device 1 having a closed end 2, that is rounded, and a collar 3 that is stretched by an elastic ring 4. At the rounded end 2 the thin-walled tubular device 1 a second elastic ring 5 is located and held in position by a means for affixing the ring 6. In this figure the means for affixing the ring is a small square of flexible material that is affixed on two of its edges to the thin-walled tubular device 1. In this manner the small square of flexible material is adapted to allow the second elastic ring 5 to pass freely through an open passage between the center of the square of flexible material and the thin-walled tubular device 1 that is covered by the square of flexible material 6. The means for affixing the ring serves to maintain the thin-walled tubular device 1 in the vagina. The thin-walled tubular device of this figure functions as a female condom-like device.

In FIG. 2a the tubular element 1 can be enclosed at the closed end by a thin cylindrical sheathing (not shown) which is axially movable in relation to the tubular element 1. However, the tubular protective device does not ordinarily have both a sheathing and a second elastic ring 5 at the same time.

Figure 2B:
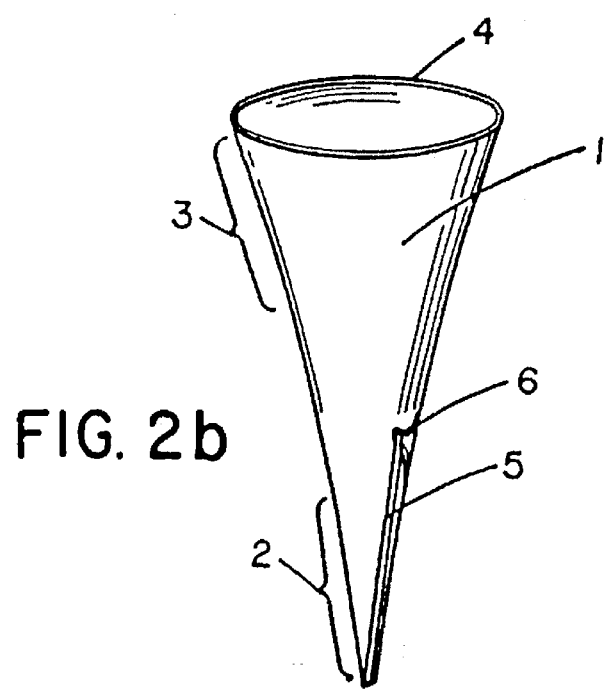

FIG. 2b discloses a side view of the thin-walled tubular device 1 of FIG. 2a. In this figure the structural and spatial arrangement at the closed end 2 of the second ring 5 and the square of flexible material 6 is depicted so as to illustrate the passage through which the second ring 5 is free to move. The second ring 5 in this embodiment is not in a planar position that is parallel to the planar position of the first ring 4. This planar position of the second ring 5 is at an acute angle to the planar position of the-first ring 4 in this embodiment because the opening-of the uterus is positioned at a similar angle to the vulva.

The diameter of the internal or second ring 5 is typically smaller that the diameter of the first ring 4. The diameter of the second ring 5 can vary to include any size that can adequately maintain the closed end 2 in the vagina. In this manner the female condom-like device can be inserted into the vagina and worn for a significant period of time before coitus. Desirable outer diameters for the second ring 5 are those typically used for diaphrams which are between about 65 millimeters and 80 millimeters.

Figure 3:
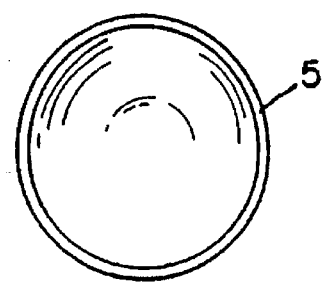
FIG. 3 is a top plan view of a closed end or internal ring for use with the protective device of FIG. 1.

FIG. 3 is a top plan view of the internal of second ring 5 of FIG. 2b. In desirable embodiments of the invention the second ring 5 is not attatched to the flexible wall of the thin-walled tubular device 1. In such embodiments the thin-walled tubular device of FIG. 1 can be provided with, but separately from, the second ring 5. In this manner the invention can be adapted for use either as a male or female condom-like device after its purchase. The thin-walled tubular device 1 can be used as a male condom-like device without a second ring 5. The thin-walled tubular device 1 can be adapted for use as a female condom-like device by inserting the second ring 5 into the closed end 2 of the thin-walled tubular device 1.

Figure 4A:
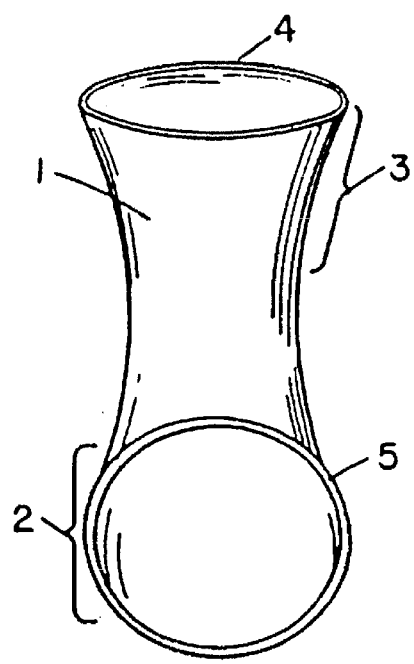
FIG. 4a is a three dimensional front view of the protective device of FIG. 1 with the closed end or internal ring of FIG. 3 inserted therein.

FIG. 4a depicts a front view of the thin-walled tubular device 1 of FIG. 1 with the internal or second ring 5 of FIG. 3 inserted into the closed end 2. This represents the preferred embodiment of the invention. The second ring 5 is inserted into the closed end 2 by sqeezing it to form an oval shape and then inserting the second ring 5 into the thin-walled tubular device 1. When the second ring 5 is released, it regains its circular shape. When the second ring 5 is in place, the thin-walled tubular device 1 can be inserted into the vagina by using the second ring 5 to function in a manner similar to a diaphram.

Figure 4B:
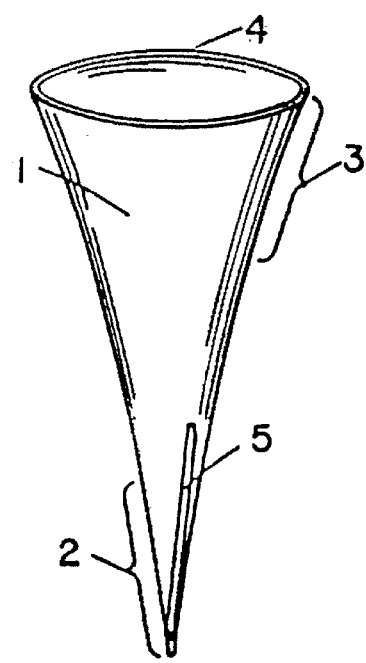
FIG. 4b is a three dimensional side view of the protective device of FIG. 1 with the closed end or internal ring of FIG. 3 inserted therein.

FIG. 4b depicts a side view of the thin-walled tubular device 1 of FIG. 1 with the internal or second ring 5 of FIG. 3 inserted into the closed end 2.

I claim:

1. A tubular protective device for protection against a transfer of infectious matter during sexual intercourse, said protective device comprising;

(a) a flexible polyurethane tube having a continuous thickness between 20 and 60 microns and having;
   (i) a closed end,
   (ii) an open end, and
   (iii) a first diameter of said tube sufficiently large to permit movement of a penis within said tube during coitus;

(b) an outwardly extending polyurethane ring for radially stretching said open end, said outwardly extending polyurethane ring having a second diameter at least equal to said first diameter and welded to said open end of said flexible polyurethane; and (c) a circular elastic ring-like member located in said closed end of said flexible, thin-walled tube having a diameter sufficient to maintain said circular elastic member in a vagina of a user.

2. The tubular protective device of claim 1 wherein said circular elastic ring member is affixed to said flexible, thin-walled tube.

* * * * *